United States Patent [19]

Irikura et al.

[11] Patent Number: 4,556,715

[45] Date of Patent: Dec. 3, 1985

[54] NICOTINIC ACID DERIVATIVES

[75] Inventors: Tsutomu Irikura, Tokyo; Seigo Suzue, Kuki; Kodo Okada, Yono, all of Japan

[73] Assignee: Kyorin Pharmaceutical Co., Ltd., Tokyo, Japan

[21] Appl. No.: 544,897

[22] Filed: Oct. 24, 1983

Related U.S. Application Data

[63] Continuation of Ser. No. 327,201, Dec. 3, 1981, abandoned.

[30] Foreign Application Priority Data

Dec. 19, 1980 [JP] Japan .................................. 55-180751

[51] Int. Cl.$^4$ ........................................... C07D 213/80
[52] U.S. Cl. .................................................. 546/322
[58] Field of Search ........................................ 546/322

[56] References Cited

U.S. PATENT DOCUMENTS

4,042,594  8/1977  Irikura ................................. 546/322

Primary Examiner—Robert W. Ramsuer
Attorney, Agent, or Firm—Armstrong, Nikaido, Marmelstein & Kubovcik

[57] ABSTRACT

This invention relates to compounds, 4-(4-substituted phenylalkyloxy) phenylalkyl nicotinates, represented by the following structural formula I and its salts, the methods for preparations thereof.

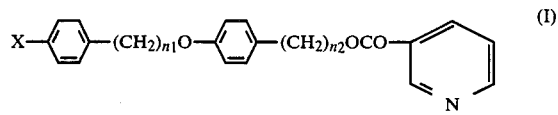

wherein $n_1$ is an integer from 2 to 6 inclusive, provided that $n_1$ and $n_2$ are not 1 at the same time, $n_1$ is an integer from 1 to 6 inclusive, and X means chlorine or fluorine atom.

2 Claims, No Drawings

NICOTINIC ACID DERIVATIVES

This is a continuation of application Ser. No. 327,201, filed Dec. 3, 1981, now abandoned.

DETAILED DESCRIPTION OF THE INVENTION

This invention relates to novel 4-(4-substituted phenylalkyloxy)phenylalkyl nicotinates and its salts, and to the method for preparation thereof. The present inventors reported previously a method for preparation of nicotinic acid 4-(4-chlorobenzyloxy)benzyl ester on Japanese patent application, and the application has been matured into Japanese Pat. no. 987237. Now, in the series of investigation for development of hypolipidemic agents, we have discovered that 4-(4-substituted phenylalkyloxy)phenylalkyl nicotinate derivatives have same or more highly remarkable hypolipidemic actions than that of the above-mentioned compound.

The preparation of the compounds of the present invention proceeds according to the following equation:

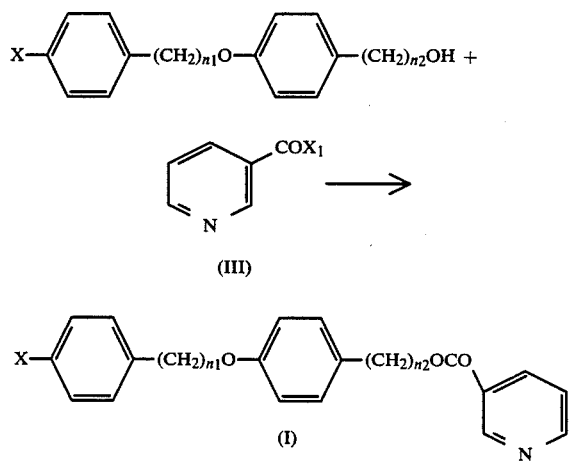

wherein $n_1$, $n_2$ and X are defined as above and $X_1$ means chlorine or bromine atom. That is, the compounds having the formula I are obtained by reaction of compounds (II), 4 (4-substituted phenylalkyloxy)phenylalkyl alcohol with one molecular or more equivalents of compounds (III), nicotinoyl halide or its hydrohalide in an organic solvent in the presence of a base at temperature between 0° C. and 150° C. The solvent can be applied, for example, benzene, toluene, N,N-dimethyl formamide, chloroform, tetrahydrofuran and the like. The base can be applied, for example, pyridine, N,N-dimethylaniline, triethylamine and the like.

These compounds are also prepared according to the following equation:

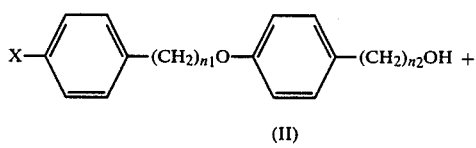

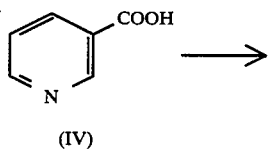

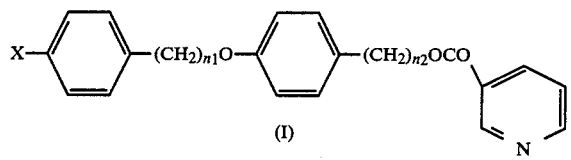

wherein $n_1$, $n_2$ and X are defined as above.

That is, the compounds having the formula I are obtained by reaction of compounds (II) with compound (IV) in the presence of an acid halide and a base. The acid halide can be applied, for example, benzenesulfonyl chloride, p-toluenesulfonyl chloride, phosphorous oxychloride, cyanuric chloride and the like. The base can be applied, for instance sodium hydroxide, potassium hydroxide, pyridine, triethylamine and the like. We suppose that the base acts as a acid-binding agents, therefore, liquid amine is used conveniently for its actions not only as a basic agent, but also as a solvent. And also, the non-polar organic solvent such as benzene, toluene and the like can be applied.

The starting compounds (II) of this invention are obtained easily from the corresponding carboxylic acid ester by reduction with sodium bis(2-methoxyethoxy)aluminium hydride, or from the corresponding aldehyde by reduction with sodium borohydride.

The compounds (I) of the present invention, obtained in this way, possess some excellent hypolipidemic actions as illustrated below, and are useful as a hypolipidemic agent.

(1) Effects on relative liver weight, serum and liver lipid levels in normal rats Male Wistar strain rats, weighing 180–210 g were orally administered the present compounds (X=Cl, $n_1=2, 3, 4$ and $n_2=1$) and 4-(4-chlorobenzyloxy)benzyl nicotinate (KCD-232), being X=Cl, $n_1=1$, $n_2=1$, respectively, which were suspended in 0.5% carboxymethyl cellulose (CMC) solution once a day at a dose of 100 mg/kg b.w. for 7 days. The last administration was occured in rats fasted overnight. At 4 hr later blood was withdrawn from jugular vein, clotted and centrifuged to obtain serum. The liver was rapidly removed and weighed. Total lipids were extracted from the serum and liver, and cholesterol (Ch), triglycerides (TG) and phospholipids (PL) levels were determined.

As shown in Table 1, the present compounds, X=Cl, $n_2=1$, $n_1=2, 3$ and 4 respectively, significantly reduced serum Ch, TG and PL compared with control administered 0.5% CMC solution alone. Additionally the compounds of the present invention falled remarkably serum lipid levels than KCD-232 used as a reference standard. It was recognized that the more increment of integer $n_1$ was, the more the lipid lowering effects of these compounds were. These compounds also scarcely induced to the hepatomegaly regardless of the increment of integer $n_1$. While in liver lipid levels, Ch, TG and PL tend to fall in proportion to the increment of integer $n_1$, especially when the last administration was carried out in rats fasted overnight KCD-232 remarkably rose liver TG level. However the present compound, being $X=Cl$, $n_1=4$, $n_2=1$, reduced TG level by 32% ($p<0.05$) compared with the control. Thus, it was clearly recognized that in proportion to the increment of integer $n_1$, the present compounds showed more effective in lowering serum lipid (Ch, TG and PL) levels than KCD-232.

On the other hand, the relative liver weight of rats treated with the present compounds was scarcely influenced and not difference with that of control group.

(2) Male rats of the Wistar strain weighing 160–180 g were fed a stock deit (CE-2, Japan CLEA, Tokyo) and water ad libitum. The present compounds and KCD-232 were suspended, respectively, in a 0.5% of CMC solution and give orally to rats once a day at a dose of 100 mg/kg b.w. for 10 days.

Control rats were received the 0.5% CMC solution alone. The diet was withdrawn immediately after the last administration of compounds. Animals were sacrificed by decapitation 4 hr after the last administration and blood was collected, clotted and centrifuged to obtain serum. The liver was excised quickly and weighed. Total lipids were extracted from the serum and liver, and the levels of Ch, TG and PL were determined colorimetrically.

As shown in Table 2 and 3, all the present compounds reduced significantly the concentrations of serum Ch, TG and PL. Particularly, in the compounds consisted of $X=Cl$, $n_13$, $n_2=1$ and $n_1=4$, $n_2=1$, the lipid lowering effects were superior to that of KCD-232 used as a reference standard.

(3) The present compounds and KCD-232 were orally given to male Wistar rats weighing 160–180 g once a day at a dose of 25 mg/kg b.w. for 10 days. Rats were subjected to fast for 4 hr immediately after the last administration of compounds, thereafter they were sacrificed by decapitation and blood was collected, clotted and centrifuged to obtain serum. The liver was removed quickly and weighed. Total lipids were extracted from the serum and liver, and then the levels of total Ch, TG and PL were determined with colorimetric methods.

Results obtained were shown in Table 4. In case of $n_2=1$, the rate of decrease in the levels of serum Ch, TG, PL and liver TG increases with increment of integer $n_1$ from 1 to 6 ($n_1=1, 3, 6$), that is, by the elongation of alkyl chain between phenyl and phenoxy groups. In case of $n_1=1$ the rate of decrease in the serum Ch level decreased as the integer $n_2$ increased from 1 to 6 ($n_2=1, 3, 6$), namely, as the alkyl chain elongated between phenyl and nicotinoyloxy groups. Though the levels of serum TG and PL as well as liver Ch and TG were reduced by these compounds, there was no relationship between the rate of decrease and $n_2$.

(4) Acute toxicity test

The present compounds were given to 6 week-old male mice of the ICR strain and their acute toxicity was examined. As shown in Table 5, all the present compounds has the high values of $LD_{50}$ (over 4,000 mg/kg) and were clarified to have extremely lower toxicity than that of KCD-232 ($n_1=1$, $n_2=1$).

TABLE 5

| Compound | | | |
|---|---|---|---|
| X | $n_1$ | $n_2$ | $LD_{50}$ (mg/kg, p o) |
| Cl | 1 | 1 | 345 |
| Cl | 3 | 1 | >4,000 |
| Cl | 4 | 1 | >4,000 |
| Cl | 6 | 1 | >4,000 |
| Cl | 1 | 3 | >4,000 |
| Cl | 1 | 6 | >4,000 |

TABLE 1

| | $n_1$ | $n_2$ | Relative liver weight (g/100 g b.w.) | Serum lipid levels (mg/ml) | | | Liver lipid levels (mg/g liver) | | |
|---|---|---|---|---|---|---|---|---|---|
| | | | | Ch | TG | PL | Ch | TG | PL |
| Control | | | 3.09 ± 0.13 (100) | 75.9 ± 5.3 (100) | 33.8 ± 3.8 (100) | 102.2 ± 6.6 (100) | 3.53 ± 0.14 (100) | 7.38 ± 1.48 (100) | 37.0 ± 0.5 (100) |
| KCD-232 | 1 | 1 | 3.20 ± 0.10 (104) | 58.5 ± 5.0* (77) | 23.4 ± 2.2* (69) | 77.7 ± 6.4* (76) | 3.88 ± 0.12 (110) | 21.45 ± 2.23*** (291) | 36.6 ± 0.7 (99) |
| The present compound[a] | 2 | 1 | 3.17 ± 0.10 (103) | 53.5 ± 2.2* (70) | 22.4 ± 4.3 (66) | 69.0 ± 2.7** (68) | 3.78 ± 0.10 (107) | 11.49 ± 1.65 (156) | 37.2 ± 1.5 (101) |
| | 3 | 1 | 3.20 ± 0.06 (104) | 48.4 ± 5.4** (64) | 18.0 ± 2.5** (53) | 64.4 ± 5.2** (63) | 3.57 ± 0.15 (101) | 5.95 ± 1.83 (81) | 34.1 ± 1.8 (92) |
| | 4 | 1 | 3.16 ± 0.05 (102) | 45.3 ± 3.8*** (60) | 16.0 ± 3.2*** (47) | 60.4 ± 4.8*** (59) | 3.43 ± 0.10 (97) | 5.06 ± 1.21* (69) | 30.2 ± 1.4 (82) |

[a]$X = Cl$;
*$P < 0.05$;
**$P < 0.01$;
***$P < 0.001$ (vs: Control);
mean ± S.E. (n = 6)

TABLE 2

| | $n_1$ | $n_2$ | Relative liver weight (g/100 g b.w.) | Serum lipid levels (mg/ml) | | | Liver lipid levels (mg/g liver) | | |
|---|---|---|---|---|---|---|---|---|---|
| | | | | Ch | TG | PL | Ch | TG | PL |
| Control | | | 3.86 ± 0.08 (100) | 86.7 ± 3.1 (100) | 123.7 ± 10.9 (100) | 148.5 ± 5.2 (100) | 3.04 ± 0.05 (100) | 6.32 ± 0.59 (100) | 38.1 ± 0.8 (100) |
| KCD-232 | 1 | 1 | 4.05 ± 0.05 (105) | 62.8 ± 3.0*** (72.5) | 40.5 ± 2.7*** (32.7) | 100.0 ± 4.6*** (67.3) | 3.15 ± 0.08 (103.6) | 4.00 ± 0.28** (63.3) | 37.8 ± 0.6 (99.2) |
| The present compound[a] | 2 | 1 | 3.98 ± 0.06 (103) | 66.5 ± 2.2*** (76.7) | 54.4 ± 5.0*** (44.0) | 109.9 ± 3.7*** (74.0) | 2.94 ± 0.07 (96.7) | 5.50 ± 0.59 (87.0) | 39.0 ± 0.7 (102.4) |
| | 3 | 1 | 3.89 ± 0.10 (101) | 62.3 ± 3.1*** (71.9) | 30.6 ± 2.8*** (24.7) | 96.8 ± 5.0*** (65.2) | 3.09 ± 0.15 (100.7) | 3.75 ± 0.27** (59.3) | 39.8 ± 0.8 (104.5) |
| | 4 | 1 | 4.04 ± 0.10 (105) | 58.3 ± 3.3*** (67.2) | 29.9 ± 2.3*** (24.2) | 90.5 ± 4.6*** (60.9) | 2.87 ± 0.13 (94.4) | 5.06 ± 0.69 (80.5) | 40.8 ± 0.7* (107.1) |
| | 6 | 1 | 4.17 ± 0.07* (108) | 64.7 ± 3.0*** (74.6) | 31.7 ± 2.8*** (25.6) | 97.8 ± 3.8*** (65.9) | 2.87 ± 0.08 (94.4) | 4.67 ± 0.32* (73.9) | 41.6 ± 0.5** (109.2) |
| | 1 | 2 | 4.10 ± 0.06* | 67.7 ± 3.3*** | 54.7 ± 6.5*** | 114.1 ± 4.7*** | 2.38 ± 0.10*** | 5.24 ± 0.36 | 39.9 ± 0.8 |

TABLE 2-continued

| | $n_1$ | $n_2$ | Relative liver weight (g/100 g b.w.) | Serum lipid levels (mg/ml) | | | Liver lipid levels (mg/g liver) | | |
|---|---|---|---|---|---|---|---|---|---|
| | | | | Ch | TG | PL | Ch | TG | PL |
| | | | (106) | (78.1) | (44.2) | (76.8) | (78.3) | (82.9) | (104.7) |
| | 1 | 4 | 4.44 ± 0.11*** | 65.4 ± 1.4*** | 48.9 ± 5.1*** | 114.3 ± 2.5*** | 2.13 ± 0.04*** | 6.73 ± 0.51 | 38.4 ± 0.7 |
| | | | (115) | (75.4) | (39.5) | (77.0) | (70.1) | (106.5) | (100.8) |
| | 2 | 2 | 3.97 ± 0.05 | 68.3 ± 3.7** | 48.4 ± 4.8*** | 116.2 ± 5.0*** | 2.41 ± 0.10*** | 5.32 ± 0.45 | 40.8 ± 0.3* |
| | | | (103) | (78.8) | (39.1) | (78.2) | (79.3) | (84.2) | (107.1) |
| | 4 | 4 | 3.90 ± 0.06 | 61.4 ± 3.2*** | 39.0 ± 3.2*** | 102.8 ± 4.4*** | 2.41 ± 0.08*** | 7.11 ± 0.53 | 40.9 ± 0.4* |
| | | | (101) | (70.8) | (31.5) | (69.2) | (79.3) | (112.5) | (107.3) |

$(a)$X = Cl;
*P < 0.05;
**P < 0.01;
***P < 0.001 (VS: Control);
Mean ± S.E. (n = 9)

TABLE 3

| | $n_1$ | $n_2$ | Relative liver weight (g/100 g b.w.) | Serum lipid levels (mg/ml) | | | Liver lipid levels (mg/g liver) | | |
|---|---|---|---|---|---|---|---|---|---|
| | | | | Ch | TG | PL | Ch | TG | PL |
| Control | | | 3.79 ± 0.06 | 97.3 ± 3.4 | 125.6 ± 13.7 | 155.8 ± 6.0 | 2.32 ± 0.13 | 7.18 ± 0.56 | 36.2 ± 0.3 |
| | | | (100) | (100) | (100) | (100) | (100) | (100) | (100) |
| KCD-232 | 1 | 1 | 3.71 ± 0.07 | 68.3 ± 3.1*** | 45.3 ± 3.5***+ | 96.8 ± 3.4*** | 2.39 ± 0.07 | 4.67 ± 0.42** | 36.1 ± 0.4 |
| | | | (98) | (70.0) | (36.1) | (62.1) | (103.0) | (65.2) | (99.7) |
| The present compound$(a)$ | 1 | 2 | 3.80 ± 0.07 | 69.2 ± 3.9*** | 34.2 ± 2.9*** | 100.8 ± 4.5*** | 2.46 ± 0.14 | 56.7 ± 0.72 | 37.5 ± 0.4 |
| | | | (100) | (70.9) | (27.3) | (64.7) | (106.0) | (79.0) | (103.6) |
| | 1 | 3 | 3.70 ± 0.05 | 81.7 ± 2.7** | 123.7 ± 5.5** | 2.27 ± 0.09 | 5.24 ± 0.40 | 34.8 ± 0.5 | |
| | | | (98) | (83.7) | (63.3) | (79.4) | (97.8) | (73.0) | (96.1) |
| | 1 | 4 | 3.91 ± 0.10 | 74.2 ± 2.5*** | 37.6 ± 3.0*** | 106.2 ± 3.6*** | 2.51 ± 0.11 | 7.42 ± 0.88 | 36.7 ± 0.9 |
| | | | (103) | (76.0) | (29.9) | (68.2) | (108.2) | (103.3) | (101.4) |
| | 1 | 6 | 3.72 ± 0.06 | 73.5 ± 2.3*** | 40.3 ± 3.5*** | 107.2 ± 3.1*** | 2.48 ± 0.10 | 6.01 ± 0.76 | 38.5 ± 0.7* |
| | | | (98) | (75.3) | (32.1) | (68.9) | (106.9) | (83.7) | (106.4) |
| | 4 | 2 | 4.03 ± 0.07* | 72.2 ± 1.3*** | 31.3 ± 3.6*** | 104.5 ± 3.7*** | 2.28 ± 0.09 | 5.72 ± 0.40 | 39.6 ± 0.9* |
| | | | (106) | (74.0) | (24.9) | (67.1) | (98.3) | (79.7) | (109.4) |
| | 6 | 6 | 3.84 ± 0.10 | 77.4 ± 3.8** | 29.8 ± 1.5*** | 101.1 ± 3.7*** | 2.38 ± 0.08 | 4.62 ± 0.15** | 38.7 ± 0.8* |
| | | | (101) | (79.3) | (23.7) | (64.9) | (102.6) | (64.3) | (106.9) |

$(a)$X = Cl;
*P < 0.05;
**P < 0.01;
***P < 0.001 (VS: Control)
Mean ± S.E. (n = 9)

TABLE 4

| | $n_1$ | $n_2$ | Relative liver weight (g/100 g b.w.) | Serum lipid levels (mg/ml) | | | Liver lipid levels (mg/g liver) | | |
|---|---|---|---|---|---|---|---|---|---|
| | | | | Ch | TG | PL | Ch | TG | PL |
| Control | | | 3.54 ± 0.04 | 78.4 ± 4.8 | 37.8 ± 4.0 | 108.2 ± 3.3 | 3.25 ± 0.16 | 7.44 ± 0.92 | 38.0 ± 1.0 |
| | | | (100) | (100) | (100) | (100) | (100) | (100) | (100) |
| KCD-232 | 1 | 1 | 3.72 ± 0.07* | 63.5 ± 3.1 | 31.3 ± 2.9 | 89.0 ± 4.4** | 2.98 ± 0.08 | 4.36 ± 0.65* | 40.2 ± 0.6 |
| | | | (105) | (81.4) | (82.8) | (82.3) | (91.7) | (58.6) | (105.8) |
| The present compound$(a)$ | 3 | 1 | 3.84 ± 0.13 | 60.3 ± 5.3* | 24.2 ± 2.8* | 83.2 ± 8.5* | 3.16 ± 0.13 | 3.97 ± 0.35** | 40.3 ± 0.9 |
| | | | (109) | (76.9) | (64.0) | (76.9) | (97.2) | (53.4) | (106.1) |
| | 6 | 1 | 3.91 ± 0.08*** | 54.2 ± 4.9** | 24.0 ± 2.1* | 72.2 ± 5.6*** | 3.14 ± 0.17 | 3.03 ± 0.41** | 38.9 ± 0.8 |
| | | | (111) | (69.1) | (63.5) | (66.7) | (96.7) | (40.7) | (102.4) |
| | 1 | 3 | 3.53 ± 0.08 | 66.4 ± 5.3 | 29.2 ± 1.7 | 85.8 ± 4.8** | 3.23 ± 0.17 | 3.80 ± 0.50** | 38.2 ± 0.5 |
| | | | (100) | (84.7) | (77.2) | (79.3) | (99.4) | (51.1) | (100.5) |
| | 1 | 6 | 3.91 ± 0.09** | 70.0 ± 5.5 | 33.5 ± 2.5 | 100.1 ± 5.9 | 2.83 ± 0.18 | 5.48 ± 0.93 | 38.8 ± 1.1 |
| | | | (111) | (89.3) | (88.6) | (92.5) | (87.1) | (73.7) | (102.1) |

$(a)$X = Cl;
*P < 0.05;
**P < 0.01 (VS: Control)
Mean ± S.E. (n = 7)

The following examples illustrate this invention in detail without, however, restricting it thereto.

EXAMPLE 1

4-[2-(4-Chlorophenyl)ethoxy]benzyl nicotinate

A mixture of 2.1 g (0.008 mole) of 4-[2-(4-chlorophenyl)ethoxy]phenylmethanol and 10.1 g triethylamine is added to a mixture of 2.1 g (0.02 mole) of hydrochloride of nicotinoyl chloride in 50 ml of anhydrous benzene with stirring and the mixture is refluxed for 12 hrs. Thereupon, the solvent is distilled off in vacuo, and water is added. The product is extracted with chloroform and the extract is washed with water and dried over sodium sulfate. Chloroform is removed and the residual solid is recrystallized from a mixture of ethanol and n-hexane to give a title compound in yield of 2.1 g (71.4%).

mp: 77°–78° C.
IR$\nu_{max}^{KBr}$(cm$^{-1}$) 2930, 1719, 1277, 1255;
MS m/e 367(M$^+$) 332(M-Cl)$^+$;

$^1$H NMR(CDCl$_3$) δ(ppm) 3.07 (t 2H), 4.18(t 2H), 5.33(s 2H), 6.88(d 2H), 7.23(s 4H), 7.37(d 2H), 8.30(d 1H), 8.77(d 1H), 9.25(s 1H);

|  | C | H | N |
|---|---|---|---|
| Anal. Calcd. for C$_{21}$H$_{18}$NO$_3$Cl: | 68.57 | 4.93 | 3.81 |
| Found: | 68.45 | 4.76 | 3.78 |

EXAMPLE 2

4-[3-(4-Chlorophenyl)propoxy]benzyl nicotinate

A mixture of 2.0 g (0.007 mole) of 4-[3-(4-chlorophenyl)propoxy)-phenylmethanol and 4.0 g triethylamine is added to 3.6 g (0.02 mole) of hydrochloride of nicotinoyl chloride in 50 ml of anhydrous benzene with stirring and the mixture is refluxed for 4 hrs. After cooling, water is added to the reaction mixture. The product is extracted with benzene and the extract is washed with water and dried over sodiun sulfate. Benzene is removed, the residual solid is recrystallized from ethanol to give a title compound in yield of 1.8 g (67.3%).
mp: 67°-68° C.
IRν$_{max}^{KBr}$(cm$^{-1}$) 2920, 1720, 1267, 1253;
MS m/e 381(M+), 346(M-Cl)+;
$^1$H NMR (CDCl$_3$) δ(ppm) 2.06(m 2H), 2.78(t 2H), 3.93(t 2H), 5.31(s 2H), 6.88(d 2H), 7.10(d 2H), 7.23(d 2H), 7.37(d 2H), 8.30(d 1H), 8.77(d 1H), 9.26(s 1H);

|  | C | H | N |
|---|---|---|---|
| Anal. Calcd. for C$_{22}$H$_{20}$NO$_3$Cl: | 69.20 | 5.28 | 3.67 |
| Found: | 68.92 | 5.18 | 3.72 |

EXAMPLE 3

4-[4-(4-chlorophenyl)butoxy]benzyl nicotinate

A mixture of 6.0 g (0.02 mol) of 4-[4-(4-chlorophenyl)butoxy]phenylmethanol and 20.2 g triethylamine is added to 5.3 g(0.03 mol) of hydrochloride of nicotinoyl chloride in 100 ml anhydrous benzene with stirring and the mixture is refluxed for 20 hrs. Thereupon, the solvent is distilled off in vacuo, and water is added. The product is extracted with chloroform and the extract is washed with water and dried over sodium sulfate. Chloroform is removed, the residual oil is purified by chromatography on silica gel to give a title compound in yield of 5.5 g (69.5%).
mp: 59°-61° C.
IRν$_{max}^{KBr}$(cm$^{-1}$) 2935, 1725, 1278, 1247;
MS m/e 395(M+), 360(M-Cl)+;
$^1$H NMR (CDCl$_3$) δ(ppm) 1.73(m 4H), 2.58(m 2H), 3.92(m 2H), 5.27(s 2H), 6.87(d 2H), 7.07(d 2H), 7.17(d 2H), 7.35(d 2H), 8.23(d 1H), 8.07(d 1H), 9.20(s 1H);

|  | C | H | N |
|---|---|---|---|
| Anal. Calcd. for C$_{23}$H$_{22}$NO$_3$Cl: | 69.78 | 5.60 | 3.54 |
| Found: | 69.80 | 5.55 | 3.51 |

EXAMPLE 4

4-(4-Chlorobenzyloxy)phenethyl nicotinate

Benzenesulfonyl chloride (10.6 g, 0.06 mole) is dropped with stirring at 60° C. to a nicotinic acid in 30 ml of pyridine to yield uniform solution. After the solution was stirred at 50°-60° C. for ten minutes, 4-(4-chlorobenzyloxy)phenyl ethanol (13.1 g, 0.05 mole) is added to the solution, and the mixture is stirred for 45 minutes at room temperature. The reaction mixture is poured into 300 ml of ice water to give crystals. The crystals are dissolved into 300 ml of chloroform, the chlorofrom layer is washed with 5% pottassium carbonate solution and water. The chloroform layer is dried over sodium sulfate, and the chloroform is evaporated to give crude crystals. The crude crystals are recrystallized from isopropanol to obtain 15.5 g (84.3%) of a title compound.
mp: 109°-110° C.

|  | C | H | N |
|---|---|---|---|
| Anal. Calcd. for C$_{21}$H$_{18}$NO$_3$Cl: | 68.57 | 4.93 | 3.81 |
| Found: | 68.63 | 4.73 | 3.89 |

EXAMPLE 5

4-(4-Chorophenethyloxy)phenetyl nicotinate

This compound is prepared, in accordance with the method of operation of Example 4, by replacing the 4-(4-chlorobenzyloxy)-phenyl ethanol with the equivalent amount (13.8 g) of 4-(4-chlorophenethyloxy)-phenethyl alcohol. Crude crystals are recrystallized from isopropanol to give 12.5 g(65.5%) of a title compound.
mp: 81°-82° C.

|  | C | H | N |
|---|---|---|---|
| Anal. Calcd. for C$_{22}$H$_{20}$NO$_3$Cl: | 69.20 | 5.28 | 3.67 |
| Found: | 69.19 | 5.19 | 3.95 |

EXAMPLE 6

4-[3-(4-Chlorophenyl)propoxy]benzyl nicotinate

This compound is prepared by the same manner described in Example 4 using the equivalent amount (13.8 g) of 4-(4-chlorophenylpropoxy)benzyl alcohol instead of 4-(4-chlorobenzyloxy)phenyl ethanol. Crude crystals are recrystallized from isopropanol to yield 15 g (78.9%) of a title compound.
mp: 69°-70° C.

|  | C | H | N |
|---|---|---|---|
| Anal. Calcd. for C$_{22}$H$_{20}$NO$_3$Cl: | 69.20 | 5.28 | 3.67 |
| Found: | 69.12 | 5.18 | 3.89 |

EXAMPLE 7

3-[4-(4-Chlorobenzyloxy)phenyl]propyl nicotinate

This compound is prepared by the same procedure of Example 4 using 13.8 g (0.05 mole) of 3-[4-(4-chlorobenzyloxy)phenyl]propanol instead of 4-(4-chlorobenzyloxy)phenyl ethanol. Obtaining crude crystals are recrystallized from isopropanol to give 17 g (89.5%) of a title compound.
mp: 109°-110° C.

|  | C | H | N |
|---|---|---|---|
| Anal. Calcd. for C$_{22}$H$_{20}$NO$_3$Cl: | 69.20 | 5.28 | 3.67 |

EXAMPLE 8

4-[4-(4-Chlorophenyl)butoxy]benzyl nicotinate

This compound is prepared by operating as in Example 4 using 14.5 g (0.05 mole) of 4-[4-(4-chlorophenyl)butoxy]benzyl alcohol instead of 4-(4-chlorobenzyloxy)phenyl ethanol. Resulting crude crystals are recrystallized to give 13.4 g(67.7%) of a title compound.
mp: 60°–61° C.

|  | C | H | N |
|---|---|---|---|
| Anal. Calcd. for $C_{23}H_{22}NO_3Cl$: | 69.78 | 5.60 | 3.54 |
| Found: | 60.96 | 5.47 | 3.74 |

EXAMPLE 9

4-[4-(4-Chlorophenyl)butoxy]phenethyl nicotinate

Benzenesulfonyl chloride (7.66 ml, 0.06 mole) is added with stirrin to a 9.2 g (0.075 mole) of nicotinic acid in 30 ml of pyridine, and then 15.2 g (0.05 mole) of 4-(4-chlorophenylbutoxy)phenethyl alcohol is added to the solution. The mixture is stirred as discribed in Example 1. The reaction mixture is poured into water, and extracted with chloroform, the chloroform layer is washed with potassium carbonate solution and water. The chloroform is removed to give a red-syrup. The red-syrup is purified by chromatography on silica gel using a mixture of benzene and chloroform (1:1) as eluent, to give 11 g (53.6%) of a title compound.

|  | C | H | N |
|---|---|---|---|
| Anal. Calcd. for $C_{24}H_{24}NO_3Cl$: | 70.32 | 5.90 | 3.42 |
| Found: | 70.38 | 5.63 | 3.67 |

EXAMPLE 10

6-[4-(4-Chlorobenzyloxy)phenyl]hexyl nicotinate

The same procedure was described in Example 4 is followed for preparing of this compound, by replacing the 4-(4-chlorobenzyloxy)phenyl ethanol with the equivalent amount (15.9 g) of 4-(4'-chlorobenzyloxy)phenyl hexanol. Obtaining crude crystals are recrystallized from ethanol to yield 13.5 g (63.7%) of a title compound.
mp: 66°–67° C.

|  | C | H | N |
|---|---|---|---|
| Anal. Calcd. for $C_{25}H_{26}NO_3Cl$: | 70.83 | 6.18 | 3.30 |
| Found: | 70.85 | 5.99 | 3.48 |

EXAMPLE 11 4-[4-Chlorobenzyloxy)phenyl]butyl nicotinate

This compound is prepared in the same way described in Example 4, except using 14 g (0.05 mole) of 4-[4-(4-chlorobenzyloxy)phenyl]butanol instead of 2-[4-(4-chlorobenzyloxy)phenyl]ethanol Resulting crude crystals are recrystallized from ethanol to give 13 g (67%) of a title compound.
mp: 75°–77° C.

|  | C | H | N |
|---|---|---|---|
| Anal. Calcd. for C H NO Cl: | 69.78 | 5.60 | 3.54 |
| Found: | 69.75 | 5.38 | 3.70 |

EXAMPLE 12

4-{4-[4-(4-Chlorophenyl)butoxy]phenyl}butyl nicotinate

The reaction for preparing of this compound is carried out in the same way described in Example 4 except using 16.6 g (0.05 mole) of 4-{4-[4-(4-chlorophenyl)butoxy]phenyl}butanol instead of 2-[4-(4-chlorobenzyloxy)phenyl]ethanol. The reaction mixture is poured into ice water, and extracted with chloroform, the chloroform layer is washed with water, diluted hydrochloric acid, potassium carbonate solution and water, respectively. Chloroform is removed to give slight yellowish syrup. The syrup is purified by chromatography to yield 9 g (41%) of a title compound.

|  | C | H | N |
|---|---|---|---|
| Anal. Calcd. for $C_{26}H_{28}NO_3Cl$: | 71.30 | 6.44 | 3.20 |
| Found: | 71.37 | 6.42 | 3.45 |

EXAMPLE 13

4-[6-(4-Chlorophenyl)hexyloxy]benzyl nicotinate

This compound is prepared by the same method described in Example 4 using 16 g (0.05 mole) of 4-[6-(4-chlorophenyl)hexyloxy]benzyl alcohol instead of 2-[4-(4-chlorophenyl)phenyl]ethanol. Resulting crude crystals are recrystallized from ethanol to give 9 g (42%) of a title compound.
mp: 56°–57° C.

|  | C | H | N |
|---|---|---|---|
| Anal. Calcd. for $C_{25}H_{26}NO_3Cl$: | 70.83 | 6.18 | 3.30 |
| Found: | 70.75 | 5.91 | 3.41 |

EXAMPLE 14

6-{4-[6'-(4-Chlorophenyl)hexyloxy]phenyl}hexyl nicotinate

This compound is prepared by the same procedure described in Example 12 using 19.5 g (0.05 mole) of 6-{4-[6-(4-Chlorophenyl)hexyloxy]phenyl}hexanol instead of 4-{4-[4-(4-chlorophenyl)butoxy]phenyl} butanol. Obtaining crude slight yellowish syrup is purified by chromatography on alumina using a mixture of benzene and n-hexane (2:1) as eluent. And resulting crystals are recrystallized from n-hexane to give 10 g (45.2%) of a title compound.
mp: 37°–40° C.

|  | C | H | N |
|---|---|---|---|
| Anal. Calcd. for $C_{25}H_{26}NO_3Cl$: | 70.83 | 6.18 | 3.30 |
| Found: | 70.75 | 5.91 | 3.41 |

-continued

|  | C | H | N |
|---|---|---|---|
| Found: | 69.17 | 5.08 | 3.77 |

What is claimed is:
1. 4-(4-(4-Halophenyl)butoxy)benzyl nicotinates having the formula:
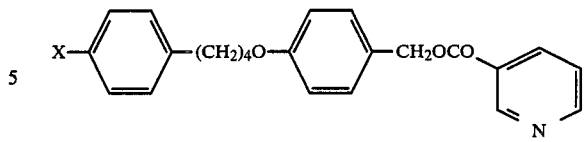
wherein X is chlorine or fluorine, and the pharmaceutically acceptable acid addition salts thereof.
2. 4-(4-(4-Chlorophenyl)butoxy)benzyl nicotinate as the compound described in claim 1.
* * * * *